(12) United States Patent
Uhrich

(10) Patent No.: US 6,497,895 B2
(45) Date of Patent: Dec. 24, 2002

(54) HYPERBRANCHED POLYMERIC MICELLES FOR ENCAPSULATION AND DELIVERY OF HYDROPHOBIC MOLECULES

(75) Inventor: Kathryn E. Uhrich, Hoboken, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/974,218

(22) Filed: Oct. 9, 2001

(65) Prior Publication Data

US 2002/0035217 A1 Mar. 21, 2002

Related U.S. Application Data

(60) Division of application No. 09/422,295, filed on Oct. 21, 1999, now Pat. No. 6,328,988, which is a continuation-in-part of application No. 09/298,729, filed on Apr. 23, 1999.

(51) Int. Cl.[7] .......................... A61F 13/00; A61K 9/27; A61K 9/48; A61K 31/74
(52) U.S. Cl. ...................... 424/422; 424/450; 424/451; 424/78.08; 514/937; 514/969
(58) Field of Search ............................... 424/422, 450, 424/451, 78.08; 514/937, 969

(56) References Cited

U.S. PATENT DOCUMENTS

| 4,573,966 A | | 3/1986 | Weikl et al. ............... 604/53 |
|---|---|---|---|
| 4,597,961 A | | 7/1986 | Etscorn ...................... 424/28 |
| 5,126,144 A | * | 6/1992 | Jaeger et al. ............... 424/448 |
| 5,132,115 A | * | 7/1992 | Wolter et al. .............. 424/448 |
| 5,830,986 A | | 11/1998 | Merrill ....................... 528/425 |
| 6,007,845 A | | 12/1999 | Domb et al. ................ 424/501 |

OTHER PUBLICATIONS

Felix, A.M., "Site–Specific Poly(ethylene glycol)ylation of Peptides", In: Poly(ethylene glycol) Chemistry and Biological Applications, ACS Symposium Series 680, J.M. Harris, et al. (Eds.), 99–115/218–225, (Apr. 1997).

Harris, J.M., et al., "ACS Symposium Series", 99–115/218–225, (Apr. 1997).

Liu, H., et al., "Hyperbranced polymeric micelles: drug encapsulation, release and polymer degradation", Department of Chemistry, Rutgers University, Piscataway, NJ, pp. 582–583,.

* cited by examiner

Primary Examiner—Thurman K. Page
Assistant Examiner—Blessing Fubara
(74) Attorney, Agent, or Firm—Schwegman, Lundberg, Woessner & Kluth, P.A.

(57) ABSTRACT

Polymeric micelles for encapsulation of hydrophobic molecules are provided. Methods and formulations for delivering hydrophobic molecules to a host via these micelles are also provided. Methods of stabilizing liposomes or lipid based formulations by addition of polymeric micelles are also provided.

19 Claims, No Drawings

HYPERBRANCHED POLYMERIC MICELLES FOR ENCAPSULATION AND DELIVERY OF HYDROPHOBIC MOLECULES

This application is a divisional of U.S. patent application Ser. No. 09/422,295. filed Oct. 21, 1999 now U.S. Pat. No. 6,328,988 which is a continuation-in-part of U.S. application Ser. No. 09/298,729, filed Apr. 23, 1999.

FIELD OF THE INVENTION

The present invention relates to new hyperbranched colloidal polymers with micellar properties. The polymers comprise a mucic acid, alkyl chains and poly(ethylene glycol). Hydrophobic molecules encapsulated within these polymeric micelles are thermodynamically stable in aqueous solutions, suspensions, dispersions, emollients, lotions, creams, salves, balms and ointments at ambient, refrigerated and elevated temperatures. Further, these polymers have been found to stabilize liposomes and other lipid based structures used routinely in these types of formulations for extended periods of time such that precipitation is prevented and optical transparency is maintained. While the polymers of the present invention can be used to encapsulate and deliver any hydrophobic molecule, these colloids are particularly useful in delivery of hydrophobic drugs via various routes and in the topical delivery of hydrophobic molecules used routinely in cosmetics, toiletries, fragrances, perfumes, skin care products and beauty aids. Such hydrophobic molecules include, but are not limited to, dyes, proteins, vitamins and fragrances.

BACKGROUND OF THE INVENTION

Micelles are a class of surfactants that form organized structures, referred to as colloidal spheres, in aqueous media. The hydrophobic shell of micelles makes the entire assembly water-soluble while the lipophilic core solubilizes hydrophobic molecules. Attempts have been made to use micelles in drug delivery applications because the lipophilic core serves as a microcontainer for drugs, thereby segregating the drugs from the outer environment by the hydrophilic segments. Micelles or colloids encapsulate the drug, shielding the body from potentially toxic levels of drug while simultaneously protecting the drug from inactivating agents in the blood and lymphatic system. Thus, solubilization of water-insoluble drugs by micelles has long been investigated as a means for improving solubility for drug delivery, in particular for parenteral or oral administration, and also for ophthalmic, topical, rectal and nasal delivery (Florence, A. Techniques of Solubilization of Drugs, Ed. Yalkowsky, S. (New York: Marcel Dekker, 1981); Atwood, D. and Florence, A. T. Pharmaceutical Aspects of Solubilization, Surfactant Systems. Their Chemistry, Pharmacy and Biology, (London: Chapman Hall, 1983):293–387).

However, the formation of micelles is both temperature- and concentration-dependent. The concentration dependency is defined as the critical micelle concentration or CMC. Thus, after micelles are injected into the bloodstream, they begin to equilibrate between the micellar, colloidal structure and individual surfactant molecules. Because of the change in micellar structure and size, control over the release of drugs within the micellar microcontainer cannot be maintained for long periods. Typically drug is released over a period of hours and this release is often inconsistent over this period. Thus, the thermodynamic equilibrium between surfactant and micelles may ultimately cause serious toxicity problems due to potentially large fluctuations in drug concentrations accompanied by the breakdown in micellar structure into surfactant molecules. This dilution is particularly large after oral and intravenous administration and can cause unwanted precipitation of hydrophobic drugs.

Thus, while micelles are frequently evaluated for use as drug delivery systems, there are only a few products on the market that are considered practical. This is due to the eventual aggregation and/or precipitation of drugs resulting from equilibration of micelles back to the monomer and the solubilization capacity being too low to be of practical use.

Attempts have been made to design non-ionic surfactants such as poly(ethylene oxide) containing molecules with improved solubilization characteristics. An early approach involved the production of large micellar systems. However, despite the increased micelle size, solubilization decreased with the longer hydrophobic chains. This decrease was attributed to deleterious changes in the poly(ethylene oxide) chains nearest to the core, the main locus of solubilization for most drugs (Elworthy, P. and Patel, M. J. Pharm. Pharmacol. 1982 34:543).

Liu et al. (Polym. Preprint., 1997 38(2):582–583) report the synthesis of a single species of hyperbranched polymeric micelles for encapsulation of small hydrophobic organic molecules. This species contains no divalent amino acid moiety. Instead, this species comprises a 1,1,1-tris (hydroxyphenyl) ethane moiety and an acylated mucic acid moiety as the divalent dicarboxylic moiety. There remains a need for suitable delivery systems for the administration of hydrophobic molecules.

SUMMARY OF THE INVENTION

This need is met by the present invention. The present invention provides new hyperbranched polymer micelles that are useful for solubilizing hydrophobic molecules in water thus greatly simplifying the preparation of aqueous formulations for delivery of such molecules.

Therefore, according to one aspect of the present invention, a polymer is provided having a structure selected from:

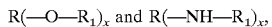

wherein $R(-O-)_x$ is a polyol moiety and $R(-NH-)_x$ is a polyamine moiety, with x being between 2 and 10, inclusive, and each $R_1$ independently has the structure:

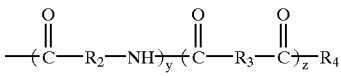

wherein

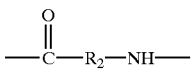

is a divalent amino acid moiety with $R_2$ being a covalent bond or having from 1 to 8 carbon atoms, and y and z are between 0 and 10, inclusive, provided that y and z are not both 0;

wherein

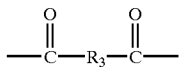

is a divalent dicarboxylic acid moiety in which $R_3$ is an alkylene or cycloalkylene group containing from 1 to about 15 carbon atoms substituted with a total of from 1 to about 10 hydroxyl groups, with at least a portion of the hydroxyl groups being acylated with 3 to 24 carbon atom carboxylic acids; and wherein $R_4$ is a poly(alkylene oxide) having the structure:

with $R_5$ being selected from 1 to 40 carbon atom alkyl groups, OH, $-OR_7$, $-NH_2$, $-NHR_7$, $-NR_7R_8$, $-CH_2-OH$, $-CH_2-OR_7$, $-CH_2-O-CH_2-R_7$, $-CH_2-NH_2$, $-CH_2-NHR_7$ and $-CH_2-NR_7R_8$;

$R_6$, $R_7$ and $R_8$ being independently selected from 2 to 40 carbon atom, straight chain or branched alkylene groups;

Q being a divalent linkage moiety; and a being between 2 and 110, inclusive;

with the proviso that when y is zero and R is a 1,1,1-tris(hydroxyphenyl) ethane moiety, the divalent dicarboxylic moiety is not an acylated mucic acid moiety.

The polymers of the present invention encapsulate a wide variety of hydrophobic molecules. The encapsulation is a physical encapsulation, and not a simple association of the hydrophobic molecule with the polymer. According to a preferred embodiment of the present invention, upon formation of the encapsulated hydrophobic molecule, the polymer is recovered and rinsed to remove any residue of non-encapsulated hydrophobic molecules.

Therefore, according to another aspect of the present invention, a hydrophobic molecule encapsulated in a polymer is provided, wherein the polymer has a structure selected from:

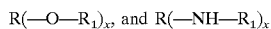

wherein $R(-O-R_1)_x$ is a polyol moiety and $R(-NH-R_1)_x$ is a polyamine moiety, with x being between 2 and 10, inclusive, and each $R_1$ independently has the structure:

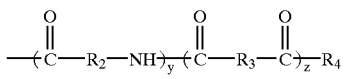

wherein

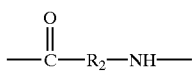

is a divalent amino acid moiety with $R_2$ being a covalent bond or having from 1 to 8 carbon atoms, and y and z are between 0 and 10, inclusive, provided that y and z are not both 0;

wherein

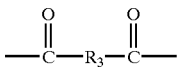

is a divalent dicarboxylic acid moiety in which $R_3$ is an alkylene or cycloalkylene group containing from 1 to about 15 carbon atoms substituted with a total of from 1 to about 10 hydroxyl groups, with at least a portion of the hydroxyl groups being acylated with 3 to 24 carbon atom carboxylic acids; and wherein $R_4$ is a poly(alkylene oxide) having the structure:

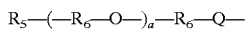

with $R_5$ being selected from 1 to 40 carbon atom alkyl groups, OH, $-OR_7$, $-NH_2$, $-NHR_7$, $-NR_7R_8$, $-CH_2-OH$, $-CH_2-OR_7$, $-CH_2-O-CH_2-R_7$, $-CH_2-NH_2$, $-CH_2-NHR_7$ and $-CH_2-NR_7R_8$;

$R_6$, $R_7$ and $R_8$ being independently selected from 2 to 40 carbon atom, straight chain or branched alkylene groups;

Q being a divalent linkage moiety; and a being between 2 and 110, inclusive;

with the proviso that when y is zero and R is a 1,1,1-tris(hydroxyphenyl) ethane moiety, the divalent dicarboxylic acid moiety is not a mucic acid moiety acylated with carboxylic acids having less than six carbon atoms.

The present invention incorporates the discovery that acylation with carboxylic acids of six carbon atoms or greater produces an unexpected increase in the affinity of the polymer interior for hydrophobic molecules. The polymers of the present invention meet the need for micellar encapsulants for hydrophobic molecules that are thermodynamically stable in aqueous media. In a preferred embodiment, the hydrophobic molecules encapsulated by the polymers are hydrophobic molecules with biological or pharmaceutical activity.

Furthermore, because the polymer encapsulates of the present invention are thermodynamically stable in aqueous media, the present invention also includes aqueous solutions, suspensions and dispersions of polymer encapsulated hydrophobic molecules. Again, the hydrophobic molecules preferably have biological or pharmaceutical activity.

The polymers of the present invention are ideal vehicles for the delivery of hydrophobic molecules to a host via a variety of administration routes, including, but not limited to orally, topically or intravenously. Accordingly, the present invention also includes formulations comprising a polymer of the present invention encapsulating hydrophobic molecules and an acceptable carrier or vehicle. In addition, the present invention includes methods of delivering a hydrophobic molecule to a host by administering to the host a formulation comprising a polymer of the present invention encapsulating hydrophobic molecules and an acceptable carrier or vehicle. Acceptable vehicles for the formulations include, but are not limited to, aqueous solutions, suspensions, dispersions, emollients, lotions, creams, salves, balms and ointments. The polymer encapsulated hydrophobic molecules can also be administered in a solid form by way of a tablet or capsule, for example, to be dissolved in the digestive tract, and, consequently, in the bloodstream. By "host" it meant to include both plants and animals including humans.

In a preferred embodiment, formulations are prepared for topical administration. The present invention incorporates the discovery that the encapsulation of hydrophobic molecules by the polymers of the present invention enhances transdermal delivery of the hydrophobic molecule. In fact, absorption through the skin can be increased by a factor of up to 1000. Preferred formulations for transdermal delivery include, but are not limited to aqueous solutions, suspensions, dispersions, aqueous gels and water-in-oil or oil-in-water emulsions. The formulations can also be applied directly to the skin as a lotion, cream or salve, or a transdermal delivery device such as a transdermal patch can be employed, in which the polymer encapsulated hydrophobic molecule is retained in the active agent reservoir of the patch. In addition to hydrophobic drugs, topical formulations are particularly useful in delivery of hydrophobic molecules including, but not limited to, dyes, proteins, vitamins and fragrances, which are used routinely in cosmetics, toiletries, fragrances, perfumes, skin care products and beauty aids.

The polymer encapsulated hydrophobic molecules may be the only active molecule in the topical formulation, or the formulation may contain the hydrophobic molecules stabilized in the formulation by other means, so that the non-encapsulated hydrophobic molecule provides a "burst effect" upon initial delivery, followed by a sustained delivery of the polymer-encapsulated molecule.

Therefore, according to another aspect of the present application, a method for transdermal delivery to an animal in need thereof of a hydrophobic molecule having biological or pharmaceutical activity is provided. An effective amount of a topical dosage form containing the hydrophobic molecule encapsulated by the polymer of the present invention and a pharmaceutically acceptable topical carrier, is applied to the skin or mucosa of the animal. Preferred polymers according to the present invention hydrolyze into components known to be biocompatible, i.e., sugars, fatty acids, amino acids and poly(ethylene glycol). This also results in low cytotoxicity of the polymer and its hydrolysis products. The poly(alkylene oxide) units enhance the immunogenicity of the encapsulate, enabling the hydrophobic molecules to evade the body's immune system, thereby increasing the circulation time of the hydrophobic molecule. This allows for effective treatment with reduced quantities of the hydrophobic molecule, which, together with the enhanced immunogenicity, prevents or reduces the severity and incidence of toxic side effects of the hydrophobic molecules.

The polymeric micelles have also been found to stabilize liposomes and other lipid-based structures for extended periods of time so that precipitation is prevented and the optical transparency of formulations is maintained. Therefore, another aspect of this invention relates to the use of these polymeric micelles in the stabilization of formulations comprising liposomes or other lipid based structures.

The above and other objects, features and advantages of the present invention will become clear from the following description of the preferred embodiment.

DETAILED DESCRIPTION OF THE INVENTION

The polymers of the present invention are prepared by coupling a plurality of hydrophobic moieties to the hydroxyl groups of a polyol core. The resulting polymer is then made water-soluble by attaching a poly(alkylene oxide) to the end of each hydrophobic moiety.

Polyols that are suitable for use as the polymer core are nearly limitless. Aliphatic polyols having from 1 to 10 carbon atoms and from 1 to 10 hydroxyl groups may be used, including ethylene glycol, alkane diols, alkyl glycols, alkylidene alkyl diols, alkyl cycloalkane diols, 1,5-decalindiol, 4,8-bis(hydroxymethyl)tricyclodecane, cycloalkylidene diols, dihydroxyalkanes, trihydroxyalkanes, and the like. Cycloaliphatic polyols may also be employed, including straight chained or closed-ring sugars and sugar alcohols, such as mannitol, sorbitol, inositol, xylitol, quebrachitol, threitol, arabitol, erythritol, adonitol, dulcitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. More examples of aliphatic polyols include derivatives of glyceraldehyde, glucose, ribose, mannose, galactose, and related stereoisomers.

Aromatic polyols are preferred because of their hydrophobicity. Among the suitable aromatic polyols are 1,1,1-tris(4'-hydroxyphenyl) alkanes, such as 1,1,1-tris(4-hydroxyphenyl)ethane, (1,3-adamantanediyl)diphenol, 2,6-bis(hydroxyalkyl)cresols, 2,2'alkylene-bis(6-t-butyl-4-alkylphenols), 2,2'-alkylene-bis(t-butylphenols), catechol, alkylcatechols, pyrogallol, fluoroglycinol, 1,2,4-benzenetriol, resorcinol, alkylresorcinols, dialkylresorcinols, orcinol monohydrate, olivetol, hydroquinone, alkylhydroquinones, 1,1-bi-2-naphthol, phenyl hydroquinones, dihydroxynaphthalenes, 4,4'-(9-fluorenylidene)-diphenol, anthrarobin, dithranol, bis (hydroxyphenyl) methane biphenols, dialkylstilbesterols, bis(hydroxyphenyl)alkanes, bisphenol-A and derivatives thereof, meso-hexesterol, nordihydroguaiaretic acid, calixarenes and derivatives thereof, tannic acid, and the like.

Other core polyols that may be used include crown ether, cyclodextrins, dextrins and other carbohydrates such as starches and amylose. Alkyl groups may be straight-chained or branched, and may contain from 1 to 10 carbon atoms.

Hydrophobic moieties are coupled to two or more of the core polyol hydroxyl groups. Preferably, all of the hydroxyl groups of the core polyol are coupled to a hydrophobic moiety.

According to one embodiment of the present invention, the hydrophobic moiety is a dicarboxylic acid moiety containing from 1 to about 10 carbon atoms and substituted with from 1 to about 10 hydroxyl groups, wherein at least a portion of the hydroxyl groups are acylated with 3 to 24 carbon atom carboxylic acids. One carboxylic acid group of the dicarboxylic acid is coupled to a hydroxyl group of the core polyol by way of an ester linkage, while the other carboxylic acid group remains free for coupling to the poly(alkylene oxide). The dicarboxylic acid may be a straight chained or branched, aliphatic or cycloaliphatic, dicarboxylic acid. Suitable aliphatic dicarboxylic acids include mucic acid, malic acid, citromalic acid, alkylmalic acid, hydroxy derivatives of glutaric acid, and alkyl glutaric acids, tartaric acid, citric acid, hydroxy derivatives of furnaric acid, and the like. Alkyl groups may be straight-chained or branched and may contain from 1 to 10 carbon atoms. The cycloaliphatic dicarboxylic acids include dicarboxylic acid derivatives of sugar alcohols.

The carboxylic acids acylating the hydroxyl groups of the dicarboxylic acids preferably contain from 6 to 24 carbon atoms. Preferably, every hydroxyl group of a dicarboxylic acid is acylated with a carboxylic acid.

The polyol coupled to two or more acylated dicarboxylic acid branches forms the hydrophobic core of the polymer of the present invention. According to another embodiment of the present invention, the volume of the cavity formed by the hydrophobic core of the polymer may be increased by inserting an amino acid or peptide linkage between the core polyol and each hydrophobic moiety. That is, a linkage as small as one amino acid up to the size of an oligopeptide containing 10 amino acid residues may be attached to each core polyol hydroxyl group or polyamine amino group, with the hydrophobic moiety being coupled to the end of the amino acid or peptide opposite the core polyol hydroxyl group or polyamine amino group.

The carboxylic acid terminus of an amino acid or peptide is coupled to a hydroxyl group of the core polyol by an ester linkage or an amino group of a core polyamine by an amide linkage. A carboxylic acid group of the acylated dicarboxylic acid is then coupled to the amine terminus of the amino acid or peptide by an amide linkage. The other carboxylic acid group again remains free for coupling to a poly (alkylene oxide). The number of amino acids employed in each peptide linkage should not be so great as to render the entire polymer water-insoluble. A peptide linkage containing from 3 to 6 amino acids is preferred. Preferred amino acids include lysine, serine, threonine, cysteine, tyrosine, aspartic acid, glutamic acid and arginine. Like the other components of the polymers of the present invention, the amino acid linkages also hydrolyze to form biocompatible degradation products.

The free carboxylic acids on the end of each hydrophobic branch on the polyol core are then coupled to a poly (alkylene oxide). The poly(alkylene oxides) are preferably coupled to the free carboxylic acids by either ester or amide linkages. The alkylene oxide units contain from 2 to 4 carbon atoms and may be straight, chained or branched. Poly(ethylene glycol) (PEG) is preferred. Alkoxy-terminated poly(alkylene oxides) are preferred, with methoxy-terminated poly(alkylene oxides) being more preferred.

The poly(alkylene oxide) preferably has between about 2 and about 110 repeating units. A poly(alkylene oxide) having between about 50 and about 110 repeating units is more preferred.

The polymers of the present invention are prepared by first acylating the hydroxyl substituted dicarboxylic acid. The dicarboxylic acid is reacted with a stoichiometric excess of the appropriate acyl chloride in the presence of a catalyst, if needed, such as $ZnCl_2$ with heating, up to the reflux temperature of the reaction mixture. Those of ordinary skill in the art will understand that the appropriate acyl chloride will have from about 2 to about 24, and preferably from about 6 to about 24, carbon atoms.

The reaction continues until substantially complete, approximately 5 hours, after which the reaction product is extracted into an ether such as diethyl ether, followed by washing of the ether fraction with water, drying and evaporation. The resulting crude product is the purified by recrystallization.

The acylated dicarboxylic acid is then coupled to a core polyol by means of a carbodiimide-mediated coupling reaction. The core polyol and a stoichiometric excess of the acylated dicarboxylic acid are dissolved in a common solvent, such as an ether, for example, diethyl ether. Carbodiimide-mediated coupling reactions are disclosed in Bodanszky, *Practice of Peptide Synthesis,* (Springer-Verlag, New York, 1984) at page 145. A quantity of a solution providing a molar equivalent of a carbodiimide and N,N-dimethylaminopyridine (DMAP) for each polyol hydroxyl group, dissolved in a common solvent such as methylene chloride, is added to the reaction mixture. The reaction proceeds rapidly to completion, after which the urea side-product corresponding to the carbodiimide is removed by suction filtration. The filtrate solution is then washed and dried, and the reaction solvent is then evaporated to recover the crude reaction product. The crude product is then purified, for example, by flash chromatography.

Carbodiimides suitable for use with the present invention include dicyclohexylcarbodiimide (DCC) 1-ethyl-3-(3-dimethylaminopropyl)carbodiimide, 1-alkyl-3-(3-dimethylaminopropyl)carbodiimide(alkyl=isopropyl, cyclohexyl), 1-cyclohexyl-3-(2-morpholinyl-(4-ethyl)) carbodiimide, 1-cyclohexyl-3-(4-diethylaminocyclohexyl) carbodiimide, 1-cyclohexyl-3-(diethylaminoethyl) carbodiimide, 1,3-di-(4-diethyl aminocyclohexyl) carbodiimide, 1-alkyl-3-(3-morpholinyl-(4-propyl)) carbodiimide (alkyl=methyl, ethyl), 1-benzyl-3-(3-dimethylamino-(N)-propyl)carbodiimide, and 1-ethyl-3-(4-azonia-4,4-dimethylpentyl)carbodiimide. In each case, the carbodiimide is used as the free base or a salt (HCl, methiodide, metho-p-toluenesulfonate, and the like). The preferred carbodiimide is DCC.

Carbodiimide-mediated coupling reactions are also used to create an amino acid or peptide linkage between the core polyol hydroxyl groups or core polyamine amino groups and the acylated dicarboxylic acids. The coupling reaction is first performed between the core polyol or polyamine and the amino acid or peptide, after which the amino acid or peptide-branched polyol or polyamine is then reacted with the acylated dicarboxylic acid in another carbodiimide-mediated coupling reaction.

The poly(alkylene oxide) chains are then attached by reacting the substituted core polyol or polyamine with an activated poly(alkylene oxide) in another carbodiimide-mediated coupling reaction. To attach the poly(alkylene oxide) chains by way of an amide linkage, poly(alkylene oxide) amines are employed. For an ester linkage, a poly (alkylene oxide) is employed. For an anhydride linkage, a poly(alkylene oxide) carboxylic acid is employed. Other linkages represented by Q in the above formulas that are suitable for use with the present invention are well known to those skilled in the pegylation art and require no further description.

A reaction mixture of the substituted core polyol and the activated poly(alkylene oxide) in a common solvent such as methylene chloride is formed. A quantity of a solution providing a molar equivalent of carbodiimide and DMAP for each substituted hydroxyl group of the core polyol, dissolved in a common solvent such as methylene chloride, is then added to the reaction mixture. The reaction mixture is maintained at room temperature with stirring for at least 12 hours, after which it is evaporated to dryness, followed by purification, for example by recrystallization, followed by flash chromatography.

The polymers of the present invention have a number average molecular weight between about 1,000 and about 100,000 daltons, measured by Gel Permeation Chromatography relative to polystyrene standards. Molecular weights between about 2,500 and about 25,000 daltons are preferred.

The resulting polymers may be used for essentially any application in which conventional micelles are employed. Examples include drug solubilization, fragrance encapsulation, passive targeting for drug delivery, waste water treatment, enhanced capillary electrophoresis activation, and induction of protein crystallization. Alkali metal cations may also be encapsulated by the polymer to form solvent-free polymer-salt complex solid electrolytes.

Polymeric micelles, unlike conventional micelles, do not have properties that are dependent on concentration or temperature. Thus, polymeric micelles do not have a CMC. Typical micelles can only encapsulate hydrophobic moieties when above the CMC and within a specific temperature range. In contrast, the polymeric systems of the present invention are useful at concentrations typically well below that of micelles in current use. For example, effective liposome stabilization has been achieved at $10^{-10}$ M. Use of the polymeric micelles to encapsulate these hydrophobic molecules thus provides multiple advantages. Specifically, the polymeric micelles act as dispersing agents for hydrophobic molecules such as dyes, fragrances, proteins, vitamins and biologically active molecules thus providing a more even distribution as compared to currently available technologies such as detergents, micelles, surfactants, fatty acids, lipids, amphiphiles and colloids. The polymeric micelles also have the ability to stabilize liposomes, emulsions, solutions, suspensions, dispersions, aqueous gels, water-in-oil or oil-in-water emulsions, and microemulsions for extended periods of time at ambient, refrigerated and elevated temperatures. Further, the spherical architecture of the polymeric micelles as opposed to agents with a linear architecture such as lipids and amphiphiles, is believed to increase lubricating ability by decreasing solution viscosity. Polymeric micelles of the present invention also have the ability to encapsulate extremely hydrophobic molecules such as lidocaine and naphthalenes. Because the hydrophobic moieties are encapsulated, they become completely water-soluble thus enhancing their absorption upon topical application. Aqueous solutions of the polymeric micelle encapsulated hydrophobic molecules are transparent and do not require addition of other solubilizing agents. Finally, the polymeric micelles have been demonstrated to be non-toxic to cells such as fibroblasts and are believed to be completely biocompatible.

According to one embodiment of the present invention, hydrophobic molecules are encapsulated by dissolving the hydrophobic molecules and the polymer in a common solvent, such as methylene chloride. The solvent is then removed, for example, by rotoevaporation. The resulting solid is then washed thoroughly with a non-polar solvent such as hexane, to remove any residual non-encapsulated hydrophobic materials. The washed solid is then thoroughly dried, preferably under vacuum, to completely remove any adsorbed solvent, and to obtain the essentially pure polymer-encapsulated hydrophobic material.

According to an alternative embodiment, the polymer of the present invention is dissolved in water, and an excess quantity of the hydrophobic material is added to the aqueous solution, with stirring. After allowing the hydrophobic material sufficient contact with the aqueous polymer solution, the excess hydrophobic material is permitted to separate from the aqueous solution, after which it is removed. The polymer-encapsulated material may then be kept in this aqueous solution, or the aqueous solution may be concentrated, or the polymer encapsulate may be recovered in dry form by evaporating the water.

When the water is evaporated, the dried polymer may be subjected to non-polar solvent rinsing to remove any residual hydrophobic material and further evaporation to remove any residual adsorbed non-polar solvent.

The present invention contemplates the use of polymer-encapsulated hydrophobic molecules at concentrations as high as 1 M and greater, up to $10^6$ M. At the same time, another advantage of the present invention is the thermodynamic stability of the polymers, which permit the formation of low concentration stable aqueous solutions of the polymer encapsulates, far below the CMCs of conventional surfactants. Stable aqueous solutions as low as $10^{-10}$ M have been obtained, although, at present, concentrations of $10^{-8}$ and greater are expected to have the greatest commercial utility. The polymers of the present invention are believed to form stable aqueous encapsulate solutions below the presently available limits of detection, i.e., below $10^{-10}$ M.

In a preferred embodiment of the present invention, the polymers are used to solubilize hydrophobic molecules with biological or pharmaceutical activity for drug delivery.

Pharmaceutical dosage forms of polymer-encapsulated hydrophobic molecules having biological or pharmaceutical activity may be formulated using physiologically acceptable carriers, excipients, stabilizers and the like, and may be provided in sustained release or timed release formulation. Acceptable carriers, excipients and diluents for therapeutic use are well known in the pharmaceutical field, and are described, for example, in *Remington's Pharmaceutical Science* (A. R. Gennaro Edit., Mack Publishing Co., 1985). Such materials are non-toxic to the recipients at the dosages and concentrations employed, and include buffers such as phosphate, citrate, acetate and other organic acid salts, antioxidants such as ascorbic acid, low molecular weight (less than about 10 residues) peptides such as polyarginine, proteins, such as serum albumin, gelatin and immunoglobulins, hydrophilic polymers such as poly(vinyl pyrrolidinone), amino acids such as glycine, glutamic acid, aspartic acid and arginine, monosaccharides, disaccharides, and other carbohydrates, including cellulose and its derivatives, glucose, mannose and dextrines, chelating agents such as EDTA, sugar alcohols such as mannitol and sorbitol, and conventional cationic and nonionic surfactants such as TWEEN, PULRONICS, and PEG.

Dosage formulations to be used for therapeutic administration must be sterile. Sterility is readily accomplished by filtration through sterile membranes, or by other conventional methods such as irradiation or treatment with gases or heat. The pH of the dosage formulations of this invention typically will be between 3 and 11, and more preferably from 5 to 9.

Hosts in need of treatment (typically mammalian) using the dosage formulations of this invention can be administered dosages that will provide optimal efficacy. The dose and method of administration will vary from subject to subject and be dependent upon such factors as the type of host being treated, and in the case of animals, its sex, weight, diet, concurrent medication, overall clinical condition, the particular hydrophobic compounds employed, the specific use for which these compounds are employed, and other factors which those skilled in the arts will recognize.

Therapeutically effective dosages may be determined by either in vitro or in vivo methods. For each particular dosage form of the present invention, individual determinations may be made to determine the optimal dosage required. The range of therapeutically effective dosages will naturally be influenced by the route of administration, the therapeutic objectives, and the condition of the host. For the various suitable routes of administration, the absorption efficiency must be individually determined for each hydrophobic compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art.

Typically, applications of compound are commenced at lower dosage levels, with dosage levels being increased until the desired effect is achieved.

A typical dosage might range from about 0.001 mg to about 1,000 mg of hydrophobic material, per kg of patient weight. Preferred dosages range from about 0.01 mg/kg to about 100 mg/kg, and more preferably from about 0.10 mg/kg to about 20 mg/kg. Advantageously, the dosage forms of this invention may administered several times daily, and other dosage regimens may also be useful.

The dosage formulations of this invention may be prepared for storage under conditions suitable for the preservation of the biological or pharmaceutical activity of the hydrophobic material, as well as for maintaining the integrity of the polymer, and are typically suitable for storage in ambient or refrigerated temperatures. The polymer encapsulates of the present invention may be formulated for administration orally, subcutaneously, intramuscularly, intravenously, colonically, rectally, nasally or intraperitonially, employing a variety of dosage forms such as solutions, tablets, capsules, gelcaps, suppositories, implanted pellets or small cylinders, aerosols and topical formulations such as lotions, ointments, drops and dermal patches. The dosage formulations of this invention are suitable for applications where localized drug delivery is desired, as well as in situations where a systemic delivery is desired.

The dosage formulations of this invention may desirably further incorporate agents to facilitate the systemic delivery of the hydrophobic material having biological or pharmaceutical activity to the desired target. The hydrophobic materials to be delivered may, in this fashion, be incorporated with antibodies, antibody fragments, growth factors, hormones, or other targeting moieties, to which the drug molecules are coupled. The present invention also contemplates the use of peptide linkages between the core polyol and the acylated dicarboxylic acids that are selected for cleavage by proteolytic enzymes, resulting in degradation of the polymer and release of the encapsulated hydrophobic material. The release of the hydrophobic material may thus be targeted by selecting a peptide sequence corresponding to a proteolytic enzyme unique to the target site, or by co-administering a proteolytic enzyme corresponding to the peptide sequence at the target site for the hydrophobic material.

However, one advantage of the polymers of the present invention is that polymer degradation is not a prerequisite for release of the hydrophobic material.

A particular class of hydrophobic molecules having biological activity that are suitable for use with the present invention are inter-cellular regulators and mediators such as interferons, growth factors, hormones, and the like. The polymers of the present invention are contemplated to be particularly effective for the efficient administration of interferons, which has proven to be problematic because of interferon's water-insolubility. As noted above, the topical dosage forms of the present invention exhibit an unexpectedly accelerated rate of transdermal delivery attributable to the encapsulation of the hydrophobic material by the polymers of the present invention. Thus, the polymer-encapsulated hydrophobic material having biological or pharmaceutical activity may be prepared as topical dosage forms such as lotions, gels, salves, creams, balms, ointments and the like. These compositions may be in the form of aqueous solutions, or in the form of oil-in-water or water-in-oil emulsions. The formulations are essentially conventional, containing well-known additives, and are prepared using art-recognized techniques.

Topical dosage forms may also be prepared by incorporating the polymer encapsulate into the reservoir of a transdermal drug delivery device. Transdermal administration systems, or "patches", are well-known in the art. Occlusive transdermal patches for the administration of an active agent to the skin or mucosa are described in U.S. Pat. Nos. 4,573,966; 4,597,961 and 4,839,164, the disclosures of which are incorporated herein by reference. Essentially any device capable of delivering an active agent transdermally may be employed to transdermally deliver the polymer encapsulate of the present invention.

As noted above, the polymer encapsulates are particularly well suited for efficient delivery through the dermis. By "efficient" it is meant that a high level of the encapsulate is evenly delivered or transported over time.

However, practically any hydrophobic therapeutic agent otherwise suitable for the practice of this invention may be employed for a variety of applications. The polymers of the present invention can also be used as thickening agents, lubricants, detergents surfactants, plasticizers and anti-fouling agents. The polymers may be used as an emulsifying, dispersing or stabilizing agent for dyes, cosmetics, pigment and pharmaceutical products. The polymers are particularly useful as an emulsifying, dispersing or stabilizing agent in the dyeing of textiles and for encapsulating dyes for cosmetics. The polymers are useful as lubricants and encapsulants for cosmetics, textiles, leathers and perfumes, and are particularly useful as a thickening agent for paints. The polymers may also be employed as an emulsifying, dispersing or stabilizing agent for components of photographic compositions and developers.

Thus, in addition to biologically or pharmaceutically active hydrophobic molecules, other hydrophobic molecules that may be encapsulated by the polymers of the present invention include insecticides, pesticides, herbicides, antiseptics, food additives, fragrances, dyes, diagnostic aids, and the like.

In a preferred embodiment, the hyperbranched polymeric micelles are used as a replacement for detergents, micelles, surfactant, fatty acids, lipids, amphiphiles, colloids and other delivery agents currently used in cosmetics, toiletries, fragrances, perfumes, skin care products and beauty aids. In this embodiment, the hyperbranched polymeric micelles are used to encapsulate hydrophobic molecules such as dyes, proteins, vitamins, biologically active molecules and fragrances which are then incorporated into aqueous solutions, suspension, dispersion, emollients, lotions, creams, salves, balms and ointment for topical delivery of these hydrophobic molecules.

Examples of hydrophobic molecules that may be encapsulated by the polymers of the present invention include, but are not limited to: abietic acid, aceglatone, acenaphthene, acenocournarol, acetohexamide, acetomeroctol, acetoxolone, acetyldigitoxins, acetylene dibromide, acetylene dichloride, acetylsalicylic acid, alantolactone, aldrin, alexitol sodium, allethrin, allylestrenol, allylsulfide, alprazolam, aluminum bis(acetylsalicylate), ambucetamide, aminochlothenoxazin, aminoglutethimide, amyl. chloride, androstenediol, anethole trithone, anilazine, anthralin, Antimycin A, aplasmomycin, arsenoacetic acid, asiaticoside, asternizole, aurodox, aurothioglycanide, 8-azaguanine, azobenzene; baicalein, Balsam Peru, Balsam Tolu, barban, baxtrobin, bendazac, bendazol, bendroflumethiazide, benomyl, benzathine, benzestrol, benzodepa, benzoxiquinone, benzphetamine, benzthiazide, benzyl benzoate, benzyl cinnamate, bibrocathol, bifenox, binapacryl, bioresmethrin, bisabolol, bisacodyl, bis(chlorophenoxy)methane, bismuth iodosubgallate, bismuth subgallate, bismuth tannate, Bisphenol A, bithionol, bornyl, bromoisovalerate, bornyl chloride, bornyl isovalerate, bornyl salicylate, brodifacoum, bromethalin, broxyquinoline, bufexamac, butamirate, butethal, buthiobate, butlated hydroxyanisole, butylated hydroxytoluene; calcium iodostearate, calcium saccharate, calcium stearate, capobenic acid, captan, carbamazepine, carbocloral, carbophenothin, carboquone, carotene, carvacrol, cephaeline, cephalin, chaulmoogric acid, chenodiol, chitin, chlordane, chlorfenac, chlorfenethol, chlorothalonil, chlorotrianisene, chlorprothixene, chlorquinaldol, chromonar, cilostazol, cinchonidine, citral, clinofibrate, clofaziminc, clofibrate, cloflucarban, clonitrate, clopidol, clorindione, cloxazolam, coroxon, corticosterone, cournachlor, coumaphos, coumithoate cresyl acetate, crimidine, crufomate, cuprobam, cyamemazine, cyclandelate, cyclarbamate cymarin, cypermethril; dapsone, defosfamide, deltamethrin, deoxycorticocosterone acetate, desoximetasone, dextromoramide, diacetazoto, dialifor, diathymosulfone, decapthon, dichlofluani, dichlorophen, dichlorphenamide, dicofol, dicryl, dicumarol, dienestrol, diethylstilbestrol, difenamizole, dihydrocodeinone enol acetate, dihydroergotamine, dihydromorphine, dihydrotachysterol, dimestrol, dimethisterone, dioxathion, diphenane, N-(1,2-diphenylethyl)nicotinamide, dipyrocetyl, disulfamide, dithianone, doxenitoin, drazoxolon, durapatite, edifenphos, emodin, enfenamic acid, erbon, ergocorninine, erythrityl tetranitrate, erythromycin stearate, estriol, ethaverine, ethisterone, ethyl biscournacetate, ethylhydrocupreine, ethyl menthane carboxamide, eugenol, euprocin, exalamide; febarbamate, fenalamide, fenbendazole, fenipentol, fenitrothion, fenofibrate, fenquizone, fenthion, feprazone, flilpin, filixic acid, floctafenine, fluanisone, flumequine, fluocortin butyl, fluoxymesterone, flurothyl, flutazolam, fumagillin, 5-furftiryl-5-isopropylbarbituric acid, fusaftmgine, glafenine, glucagon, glutethimide, glybuthiazole, griseofulvin, guaiacol carbonate, guaiacol phosphate, halcinonide, hematoporphyrin, hexachlorophene, hexestrol, hexetidine, hexobarbital, hydrochlorothiazide, hydrocodone, ibuproxam, idebenone, indomethacin, inositol niacinate, iobenzamic acid, iocetamic acid, iodipamide, iomeglamic acid, ipodate, isometheptene, isonoxin, 2-isovalerylindane-1,3-dione; josamycin, 11-ketoprogesterone, laurocapram, 3-O-lauroylpyridoxol diacetate, lidocaine, lindane, linolenic acid, liothyronine, lucensomycin, mancozeb, mandelic acid, isoamyl ester, mazindol, mebendazole, mebhydroline, mebiquine, melarsoprol, melphalan, menadione, menthyl valerate, mephenoxalone, mephentermine, mephenytoin, meprylcaine, mestanolone, mestranol, mesulfen, metergoline, methallatal, methandriol, methaqualone, methylcholanthrene, methylphenidate, 17-methyltestosterone, metipranolol, minaprine, myoral, naftalofos, naftopidil, naphthalene, 2-naphthyl lactate, 2-(2-naphthyloxy)ethanol, naphthyl salicylate, naproxen, nealbarbital, nemadectin, niclosamide, nicoclonate, nicomorphine, nifuroquine, nifuroxazide, nitracrine, nitromersol, nogalamycin, nordazepam, norethandrolone, norgestrienone;octaverine, oleandrin, oleic acid, oxazeparn, oxazolam, oxeladin, oxwthazaine, oxycodone, oxymesterone, oxyphenistan acetate, paraherquamide, parathion, pemoline, pentaerythritol tetranitrate, pentylphenol, perphenazine, phencarbamide, pheniramine, 2-phenyl-6-chlorophenol, phenthnethylbarbituric acid, phenytoin, phosalone, O-phthalylsulfathiazole, phylloquinone, picadex, pifarnine, piketopfen, piprozolin, pirozadil, plafibride, plaunotol, polaprezinc, polythiazide, probenecid, progesterone, promegestone, propanidid, propargite, propham, proquazone, protionamide, pyrimethamine, pyrimithate, pyrvinium pamoate; quercetin, quinbolone, quizalofo-ethyl, rafoxanide, rescinnamine, rociverine, ronnel; salen, scarlet red, siccanin, simazine, simetride, sobuzoxane, solan, spironolactone, squalene, stanolone, sucralfate, sulfabenz, sulfaguanole, sulfasalazine, sulfoxide, sulpiride, suxibuzone, talbutal, terguide, testosterone, tetrabromocresol, tetrandrine, thiacetazone, thiocolchicine, thioctic acid, thioquinox, thioridazine, thiram, thymyl N-isoamylcarbamate, tioxidazole, tioxolone, tocopherol, tolciclate, tolnaftate, triclosan, triflusal, triparanol; ursolic acid, valinomycin, verapamil, vinblastine, vitamin A, vitamin D, vitamin E, xenbucin, xylazine, zaltoprofen, and zearalenone.

The following non-limiting examples set forth hereinbelow illustrate certain aspects of the invention. All parts and percentages are by weight unless otherwise noted and all temperatures are in degrees Celsius. All PEGs were obtained from Shearwater Polymers (Birmingham, Ala.) and used without further purification. All other chemicals were obtained from Aldrich (Milwaukee, Wis.) and used without further purification. Analytical grade solvents were used for all the reactions. Methylene chloride, tetrahydrofuran (THF), triethylamine (TEA) and dimethylsulfoxide (DMSO) were distilled. Nuclear magnetic resonance spectroscopy ($^1$H NMR, $^{13}$C NMR), infrared spectroscopy (IR), mass spectrometry (MS), gel permeation chromatography (GPQ and elemental analysis were used for physicochemical characterization. For differential scanning calorimetry (DSC) measurements, samples were heated under dry nitrogen gas. Data were collected at heating and cooling rates of 10° C./minute with a two cycle minimum. For thermogravimetric analysis (TGA), samples were also heated under dry nitrogen gas. Data were collected at a heating rate of 20° C./minute. Molecular weights were determined by GPC relative to narrow molecular weight polystyrene standards.

EXAMPLES

Examples 1–3

Acylation of Mucic Acid

Example 1

Mucic Acid Propyl Ester

To a neat mixture of mucic acid (4.2 g, 20 mmol) and propionyl chloride (18 ml, 200 mmol) was added $ZnCl_2$ (0.28 g, 2.0 mmol). The reaction mixture was heated at reflux temperature for three hours. After cooling, diethyl ether (20 ml) was added to the reaction mixture and the solution poured onto ice chips (approximately 100 g) with stirring. Additional diethyl ether (80 ml) was added to the mixture and stirring continued for 30 minutes more. The ether portion was separated, washed with water to a neutral pH, dried over anhydrous $Na_2SO_4$ and evaporated to dryness. The crude product was purified by recrystallization from a cosolvent system of diethyl ether and methylene chloride, collected by vacuum filtration, washed by ice cold methylene chloride and dried at 105° C. (12 hours) to constant weight. A white solid having a $T_m$ of 196° C. was obtained at a 56% yield.

Example 2
Mucic Acid Hexyl Ester

Mucic acid hexyl ester was prepared as in Example 1, substituting caproyl chloride for propionyl chloride. A white solid having a $T_m$ of 171° C. was obtained at a yield of 68%.

Example 3
Mucic Acid Lauryl Ester

Mucic acid lauryl ester was prepared as in Example 1, substituting lauryl chloride for propionyl chloride. A white solid having a $T_m$ of 145° C. was obtained at a yield of 65%.

Examples 4–6
Preparation of Polymer Core

Example 4
Propyl Ester

The mucic acid propyl ester of Example 1 (6.0 mmol) and 1,1,1-tris(4'-hydroxyphenyl)ethane (0.51 g, 1.7 mmol) were dissolved in anhydrous ethyl ether (150 ml). To the reaction mixture, a solution of DCC (1.2 g, 6.0 mmol) and DMAP (0.74 g, 6.0 mmol) in 25 ml methylene chloride was added dropwise. After 15 minutes, the DCC side-product (dicyclohexylurea) was removed by suction filtration. The filtrate was washed with 20 ml portions of 0.1 N HCl(2×) and brine (4×), dried over anhydrous $Na_2SO_4$, and evaporated to dryness. The crude product was purified by flash chromatography using ethyl ether:methanol:acetic acid (90:5:5) as eluent. A white solid having a $T_m$ of 158° C. was obtained at 58% yield.

Example 5
Hexyl Ester

The hexyl ester core molecule was prepared according to the method of Example 4, substituting the mucic acid hexyl ester of Example 2 for the mucic acid propyl ester. A white solid having a $T_m$ of 147° C. was obtained at 36% yield.

Example 6
Lauryl Ester

The lauryl ester core molecule was prepared according to the method of Example 4, substituting the mucic acid lauryl ester of Example 3 for the mucic acid propyl ester. A white solid having a $T_m$ of 136° C. was obtained at yield of 33%.

Examples 7–11
Preparation of Final Polymers

Example 7
Mucic Acid Hexyl Ester Core Polymer with Triethylene Glycol (TEG) Branches To a mixture of the core molecule of Example 5 (0.106 mmol) and methoxyterminated triethylene glycol amine (0.351 mmol) in 20 ml of methylene chloride at room temperature, DCC (0.351 mmol) and DMAP (0.351 mmol) in 2 ml methylene chloride was added dropwise. After three days, the reaction mixture was evaporated to dryness, the residue dissolved into 20 ml methanol, and the crude product precipitated from 400 ml petroleum ether at room temperature. The crude product was first purified by flash chromatography using ethyl ether:methanol:acetic acid (90:5:5) as eluent, then further purified by repetitive precipitation using methylene chloride as solvent and diethyl ether/petroleum ether as non-solvent. The ratio between methylene chloride and ethers was progressively changed. A white solvent was obtained having a $T_m$ of 31° C., a $T_d$ of 220° C. and $M_w$ of 2,400 daltons at a yield of 15%.

Example 8
Mucic Acid Hexyl Ester Core Polymer with PEG 2000 Branches

A mucic acid hexyl ester core polymer with PEG 2000 branches was prepared according to the method of Example 7, substituting methoxy-terminated poly(ethylene glycol) amine ($H_2N$-m-PEG 2000, $M_w$=2000) for the methoxy-terminated triethylene glycol amine of Example 7. A white solid was obtained having a $T_m$ of 54° C. and a $M_w$ of 9,400 daltons at a yield of 25%.

Example 9
Mucic Acid Hexyl Ester Core Polymer with PEG 5000 Branches

A mucic acid hexyl ester core polymer with PEG 5000 branches was prepared according to the method of Example 7, substituting methoxy-terminated poly(ethylene glycol) amine ($H_2N$-PEG 5000, MW=5000) for the methoxy-terminated triethylene glycol amine of Example 7. A white solid having a $T_m$ of 61° C. and a $M_w$ of 17,800 daltons was obtained at 17% yield.

Example 10
Mucic Acid Propyl Ester Core Polymer with PEG 5000 Branches

Mucic acid propyl ester core polymer with PEG 5000 branches was prepared according to the method of Example 9, substituting the mucic acid propyl ester core polymer of Example 4 for the mucic acid hexyl ester core polymer. A white solid was obtained having a $T_m$ of 62° C. and a $M_w$ of 17,000 daltons at 30% yield.

Example 11
Mucic Acid Lauryl Ester Core Polymer with PEG 5000 Branches

Mucic acid lauryl ester core polymer with PEG 5000 branches was prepared according to the method of Example 9, substituting the mucic acid lauryl ester core polymer of Example 6 for the mucic acid hexyl ester core polymer. A white solid was obtained having a $T_m$ of 60° C. and a $M_w$ of 19,100 daltons at a yield of 45%.

For the polymers of Examples 8–11, TGA showed two stages of decomposition. The first stage corresponded to cleavage of the core structures from the ethylene oxide chains (about 200° C.) with the appropriate weight loss, and the second stage corresponded to decomposition of the ethylene oxide chain.

Example 12
Encapsulation Studies

Lidocaine (50 mg) and the polymer of Example 9 (50 mg) were dissolved in 2.0 ml methylene chloride. The solution was evaporated to dryness and the solid residue extensively washed with hexane until lidocaine was no longer detected in the washings. The solid was dried under vacuum at 25° C. for about 2 hours. A portion (5.0 mg) of this solid was dissolved into methanol (1.0 ml) to release the entrapped lidocaine, and the lidocaine concentration was quantified by high pressure liquid chromatography (HPLC) according to a calibration curve generated from a series of standard solutions ranging from 0.005 to 0.5 mg/ml lidocaine. The linearity of the curve indicated a direct, proportional relationship between absorbance and lidocaine concentration. Using the equation of the lidocaine calibration curve, the amount of lidocaine entrapped in the micelle core was determined. PEG with a molecular weight of 5,000 daltons was used as the HPLC control.

Encapsulation number was defined as the amount of molecules that can be entrapped within the polymeric micelles. The values for the polymers of Example 9, 10 and 11 were 1.0, 0.7 and 1.6 weight %, respectively. The encapsulation number increased as the hydrophobicity of the polymer interior increased.

The PEG arms of the polymers of the present invention thus form a hydrophilic shell that solubilizes the polymer in water, while the core forms a hydrophobic microenvironment that encapsulates small hydrophobic molecules. Unlike conventional micelles, however, the polymeric micelles of the present invention are thermodynamically stable because of the covalent linkages between the polymer arms. The ability to encapsulate small molecules, the enhanced solubility and the lack of aggregation characterize the usefulness of these polymers as drug delivery systems. Candidate drugs, of which there are many, have aromatic or heteroaromatic moieties and carbonyl functionalities (e.g., amides and carboxylates). The biocompatibility and biodegradability of these polymers further characterize their utility for drug delivery. The excellent water-solubility of these polymers makes intravenous injection and oral administration of hydrophobic drug molecules possible. For controlled release applications, the small size of these polymers, along with their enhanced thermodynamic stability, further characterizes their utility.

Example 13

Interactions with Liposomes

Fusion of biological membranes is fundamental to a number of physiological and pharmacological processes. Because fusion is affected by surfactant molecules, the colloidal polymers of the present invention were also expected to affect fusion processes. Liposomes, also referred to as vesicles, of dipalmitoyl-phosphatidylcholine (DPPC) are well characterized in the literature and frequently used as models for cell membranes (Attwood, D. and Florence, A. T. Surfactant Systems. Their Chemistry, Pharmacy and Biology, (London: Chapman Hall, 1983 293–387).

To monitor interactions of the polymeric micelle with DPPC liposome structure, microdifferential scanning calorimetry (DSC) was utilized to monitor thermotropic changes. After several days of stabilization, the DPPC vesicles showed two distinct transitions at 38° C. and 42° C. corresponding to small unilamellar vesicles (SUV) and large unilamellar vesicles (LUV), respectively. Addition of the polymeric micelle to the stabilized vesicles caused a rapid and complete shift in the DSC profile corresponding to the complete conversion of SLWs to LUVs. Further, the polymeric micelles promoted fusion processes to form more thermodynamically stable LUVs with a total enthalpy change of 12.8 cal/g. Typically, the fusion event and conversion of SUVs to LUVs is promoted by lowering the solution temperature well below the phase transition to promote defects in the SUV structures. However, these studies demonstrate that addition of the polymeric micelles forced defects in the SUV structure to enable fusion to occur at higher temperatures.

Confocal microscopy studies at 100× magnification revealed a clear difference between solutions of DPPC liposomes with and without the polymeric micelles. Differences could also be observed visually as the polymer/liposome solution was clear while the liposome solution was opaque. Further, after only one hour at room temperature, the liposomes aggregated and precipitated out of the aqueous media when the polymeric micelles were not present. By comparison, addition of the polymeric micelles to the liposome solution appeared to stabilize the liposomes such that the solution remained translucent for at least 11 months when stored at room temperature.

Using freeze fracture techniques, this stabilization was visualized using transmission electron microscopy. The average molecular size of liposomes, polymeric micelles and polymeric micelle/liposome mixtures in aqueous media was determined as the ratio between the average diameter in microns. All samples were prepared with a concentration of 2 mg/ml. In liposome solutions, two populations existed with average sizes of 0.10 μm and 0.50 μm. The average size of the polymeric micelles was 0.16 μm. When the polymeric micelles were added to the liposome solutions, only one population was observed with an average size of 0.08 μm. These results are consistent with other studies demonstrating that addition of the polymeric micelles stabilizes liposome structures.

Example 14

Polymer In Vitro Degradation

Hydrolytic degradation of polymer samples, in triplicate, was performed at 37° C. in a sodium phosphate buffer solution at pH 7.4. A small amount of the buffer solution was taken at frequent time intervals up to 12 months for analysis. Using both HPLC and GPC methods, no degradation of the polymer was observed under these storage conditions.

The enzyme papain was used to biodegrade polymeric micelles. Papain is a proteolytic enzyme with a defined structure and established properties. Function is optimal at pH 5.0 but also works in neutral and alkaline media. Papain is incompletely soluble in water, and practically insoluble in most organic solvents, which simplifies the isolation and analytical methods. Polymer degradation was monitored by following the appearance of degradation products such as mucic acid, hexanoic acid, MA(hex), tris(hydroxyphenyl) ethane and PEG by HPLC. To prepare samples for HPLC analysis, polymeric micelles were dissolved in buffered enzyme solution. At defined time intervals, the solution was extracted with ethyl ether such that the polymer and the degradation products remained in the organic phase while the enzyme remained in the aqueous solution. The organic phase was analyzed by HPLC using the refractive index detector and also evaluated by NMR and IR spectroscopies.

Results from these experiments indicate that the amide bond linking PEG to the polymer is cleaved first after two hours of incubation. The core molecule was not observed up to 24 hours but was then rapidly released. Mucic acid and hexanoic acid were not detectable using UV or RI detectors, but were observed using NMR and IR spectroscopic methods up to 24 hours.

Example 15

Evaluation of Cytotoxicity

In vitro toxicity characteristics of the polymeric micelles were examined in L-929 fibroblasts. The viability of the fibroblasts was monitored by counting live cells at 3, 7 and 21 days using polymer concentrations of $1 \times 10^{-4}$ M, $10^{-6}$ M, $10^{-7}$ M and $10^{-8}$ M. Cells which had been incubated in solutions of polymeric micelles at the highest concentration ($10^{-4}$ M) did not survive at any time point. However, controls solutions which contained only PEG also had the same effect. All fibroblasts maintained in polymer solutions of lower concentrations (from $10^{-6}$ M to $10^{-8}$ M) survived and proliferated in the observed time period.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A transdermal device for the controlled release of a biologically or pharmaceutically active agent to the skin or mucosa of an animal, said device comprising a laminate of:

a. a reservoir layer having a first surface and a second surface, and having an encapsulate of a hydrophobic molecule encapsulated in a polymer, said polymer having a structure selected from the group consisting of:

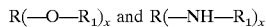

wherein $R(-O-)_x$ is a polyol and $R(-NH)_x$ is a polyamine, with x being between 2 and 10, inclusive, and each $R_x$ independently has the structure:

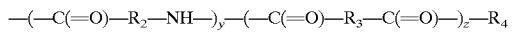

wherein $-C(=O)-R_2-NH-$ is obtained from a divalent amino acid with $R_2$ being a covalent bond or having from 1–8 carbon atoms, and y and z are between 0 and 10 inclusive, provided y and z are not both 0;

wherein $-C(=O)-R_3-C(=O)-$ is obtained from a divalent dicarboxylic acid in which $R_3$ is an alkylene or cycloalkylene group containing from 1 to 15 carbon atoms, substituted with a total of from 1 to about 10 hydroxyl groups, with at least a portion of the hydroxyl groups being acylated with from 3 to about 24 carbon atom carboxylic acids;

$R_4$ is a poly(alkylene oxide) having the structure:

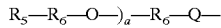

$R_5$ is selected from the group consisting of 1 to 40 carbon atom alkyl groups, $-OH$, $-OR_7$, $-NH_2$, $-NHR_7$, $-NR_7R_8$, $-CH_2-OH$, $-CH_2-OR_7$, $-CH_2-O-CH_2-R_7$, $-CH_2-NH_2$, $-CH_2-NHR_7$ and $-CH_2-NR_7R_8$;

$R_6$, $R_7$ and $R_8$ are independently selected from the group consisting of 2 to 40 carbon atom, straight-chain or branched alkylene groups, Q is a divalent linkage; and a is between 2 and 110, inclusive;

provided that when y is 0 and R is a 1,1,1-tris (hydroxyphenyl)ethane, the divalent dicarboxylic acid is not an acylated mucic acid;

b. a backing layer having an inner surface and an outer surface, wherein said second surface of said reservoir layer and said inner surface of said backing layer are laminated together so that said encapsulate cannot permeate from said second surface of said reservoir layer through said outer surface of said backing layer; and c. a pressure sensitive adhesive layer coated on said first surface of said reservoir layer for affixing said laminate to said skin or mucosa of said animal, so that said encapsulate is capable of being continuously released from said first surface of said reservoir layer thereto.

2. The device of claim 1, wherein said backing layer comprises one or more layers of an occlusive material.

3. The device of claim 1, wherein $R(-O-)_x$ is obtained from an aliphatic polyol having from 1 to 10 carbon atoms.

4. The device of claim 1, wherein $R(-O-)_x$ is obtained from a cycloaliphatic polyol.

5. The device of claim 4, wherein the cycloaliphatic polyol is a sugar.

6. The device of claim 1, wherein $R(-O-)_x$ is obtained from an aromatic polyol.

7. The device of claim 6, wherein the aromatic polyol is 1,1,1-tris(4'-hydroxyphenyl)ethane, (1,3-adamantanediyl) diphenol, 2,6-bis(hydroxyalkyl)cresol, 2,2'-alkylene-bis(6-tert-butyl-4-alkylphenol), 2-2'-alkylene-bis(t-butylphenol), catechol, an alkylcatechol, pyrogallol, fluoroglycinol, 1,2,4-benzenetriol, resorcinol, an alkylresorcinol, a dialkylresorcinol, orcinol monohydrate, olivetol, hydroquinone, an alkylhydroquinone, 1,1-bi-2-naphthol, a phenyl hydroquinone, a dihydroxynaphthalene, 4,4'-(9-fluorenylidene)-diphenol, anthrarobin, dithranol, bis (hydroxyphenyl) methane a biphenol, a dialkylstilbesterol, a bis(hydroxyphenyl) alkane, or bisphenol-A.

8. The device of claim 1, wherein $R(-O-)_x$ is obtained from a hydroxylated crown ether, a cyclodextrin, or a dextrin.

9. The device of claim 1, wherein the polymer has a number average molecular weight between about 1,000 and about 100,000 daltons.

10. The device of claim 1, wherein the polymer has a number average molecular weight between about 2,500 and about 25,000 daltons.

11. A method of stabilizing a liposome or lipid-based formulation comprising adding to the liposome or lipid-based formulation a polymer, said polymer having a structure selected from the group consisting of:

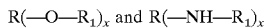

wherein $R(-O-)_x$ is obtained from a polyol and $R(-NH)_x$ is obtained from a polyamine, with x being between 2 and 10, inclusive, and each $R_1$ independently has the structure:

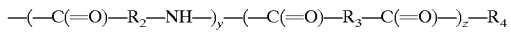

wherein $-C(=O)-R_2-NH-$ is obtained from a divalent amino acid with $R_2$ being a covalent bond or having from 1–8 carbon atoms, and y and z are between 0 and 10 inclusive, provided y and z are not both 0;

wherein $-C(=O)-R_3-C(=O)-$ is obtained from a divalent dicarboxylic acid in which $R_3$ is an alkylene or cycloalkylene group containing from 1 to 15 carbon atoms, substituted with a total of from 1 to about 10 hydroxyl groups, with at least a portion of the hydroxyl groups being acylated with from 3 to about 24 carbon atom carboxylic acids;

$R_4$ is a poly(alkylene oxide) having the structure:

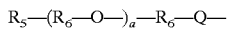

$R_5$ is selected from the group consisting of 1 to 40 carbon atom alkyl groups, $-OH$, $-OR_7$, $-NH_2$, $-NHR_7$, $-NR_7R_8$, $-CH_2-OH$, $-CH_2-OR_7$, $-CH_2-O-CH_2-R_7$, $-CH_2-NH_2$, $-CH_2-NHR_7$ and $-CH_2-NR_7R_8$;

$R_6$, $R_7$ and $R_8$ are independently selected from the group consisting of 2 to 40 carbon atom, straight-chain or branched alkylene groups, Q is a divalent linkage; and a is between 2 and 110, inclusive;

provided that when y is 0 and R is a 1,1,1-tris (hydroxyphenyl)ethane, the divalent dicarboxylic acid is not an acylated mucic acid.

12. The method of claim 11, wherein R(—O—)$_x$ is obtained from an aliphatic polyol having from 1 to 10 carbon atoms.

13. The method of claim 11, wherein R(—O—)$_x$ is obtained from a cycloaliphatic polyol.

14. The method of claim 13, wherein the cycloaliphatic polyol is a sugar.

15. The method of claim 11, wherein R(—O—)$_x$ is obtained from an aromatic polyol.

16. The method of claim 15, wherein the aromatic polyol is 1,1,1-tris(4'-hydroxyphenyl)ethane, (1,3-adamantanediyl) diphenol, 2,6-bis(hydroxyalkyl)cresol, 2,2'-alkylene-bis(6-tert-butyl-4-alkylphenol), 2-2'-alkylene-bis(t-butylphenol), catechol, an alkylcatechol, pyrogallol, fluoroglycinol, 1,2,4-benzenetriol, resorcinol, an alkylresorcinol, a dialkylresorcinol, orcinol monohydrate, olivetol, hydroquinone, an alkylhydroquinone, 1,1-bi-2-naphthol, a phenyl hydroquinone, a dihydroxynaphthalene, 4,4'-(9-fluorenylidene)-diphenol, anthrarobin, dithranol, bis (hydroxyphenyl) methane a biphenol, a dialkylstilbesterol, a bis(hydroxyphenyl) alkane, or bisphenol-A.

17. The method of claim 11, wherein R(—O—)$_x$ is obtained from a hydroxylated crown ether, a cyclodextrin, or a dextrin.

18. The method of claim 11, wherein the polymer has a number average molecular weight between about 1,000 and about 100,000 daltons.

19. The method of claim 11, wherein the polymer has a number average molecular weight between about 2,500 and about 25,000 daltons.

* * * * *

UNITED STATES PATENT AND TRADEMARK OFFICE
CERTIFICATE OF CORRECTION

PATENT NO. : 6,497,895 B2
DATED : December 24, 2002
INVENTOR(S) : Kathryn E. Uhrich Ph.D.

It is certified that error appears in the above-identified patent and that said Letters Patent is hereby corrected as shown below:

<u>Column 1,</u>
Line 6, delete "." after "09/422,295" and insert -- , -- therefor.

<u>Column 19,</u>
Line 18, delete "$R_x$" and insert -- $R_1$ -- therefor.

Signed and Sealed this

Seventh Day of October, 2003

JAMES E. ROGAN
*Director of the United States Patent and Trademark Office*